United States Patent
Kim et al.

(10) Patent No.: US 12,100,806 B2
(45) Date of Patent: Sep. 24, 2024

(54) NON-AQUEOUS ELECTROLYTE SOLUTION FOR LITHIUM SECONDARY BATTERY AND LITHIUM SECONDARY BATTERY INCLUDING THE SAME

(71) Applicant: LG Chem, Ltd., Seoul (KR)

(72) Inventors: Hyun Seung Kim, Daejeon (KR); Chul Haeng Lee, Daejeon (KR); Yu Ha An, Daejeon (KR); Jeong Woo Oh, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 885 days.

(21) Appl. No.: 17/056,948

(22) PCT Filed: Sep. 11, 2019

(86) PCT No.: PCT/KR2019/011857
§ 371 (c)(1),
(2) Date: Nov. 19, 2020

(87) PCT Pub. No.: WO2020/055180
PCT Pub. Date: Mar. 19, 2020

(65) Prior Publication Data
US 2021/0184257 A1    Jun. 17, 2021

(30) Foreign Application Priority Data
Sep. 12, 2018    (KR) .................. 10-2018-0108960

(51) Int. Cl.
*H01M 10/0566*    (2010.01)
*C07C 50/04*    (2006.01)
(Continued)

(52) U.S. Cl.
CPC ......... *H01M 10/0566* (2013.01); *C07C 50/04* (2013.01); *H01M 4/505* (2013.01);
(Continued)

(58) Field of Classification Search
CPC ............. H01M 10/0566; H01M 4/505; H01M 10/0525; H01M 2004/028; H01M 2300/0025; C07C 50/04
See application file for complete search history.

(56) References Cited

U.S. PATENT DOCUMENTS

| | | |
|---|---|---|
| 3,730,868 A | 5/1973 | Niedrach |
| 2004/0185347 A1 | 9/2004 | Kim et al. |

(Continued)

FOREIGN PATENT DOCUMENTS

| | | |
|---|---|---|
| CN | 101263622 A | 9/2008 |
| CN | 105098235 A | 11/2015 |

(Continued)

OTHER PUBLICATIONS

European Search Report for Application No. 19860402.7, dated Jul. 16, 2021, 6 pages.
(Continued)

*Primary Examiner* — Brian R Ohara
*Assistant Examiner* — Emily Elizabeth Freeman
(74) *Attorney, Agent, or Firm* — Lerner David LLP (57) ABSTRACT

A non-aqueous electrolyte solution for a lithium secondary battery and a lithium secondary battery including the same are disclosed herein. In some embodiments, a non-aqueous electrolyte solution for a lithium secondary battery, includes a lithium salt, an organic solvent, and an additive, wherein the additive includes a compound represented by Formula 1.

8 Claims, 2 Drawing Sheets

(51) Int. Cl.
*H01M 4/02* (2006.01)
*H01M 4/505* (2010.01)
*H01M 10/0525* (2010.01)

(52) U.S. Cl.
CPC .. *H01M 10/0525* (2013.01); *H01M 2004/028* (2013.01); *H01M 2300/0025* (2013.01)

(56) References Cited

U.S. PATENT DOCUMENTS

| | | | |
|---|---|---|---|
| 2004/0259002 | A1 | 12/2004 | Kim et al. |
| 2010/0129723 | A1 | 5/2010 | Noda et al. |
| 2016/0197371 | A1* | 7/2016 | Takechi ............ H01M 8/188 429/418 |
| 2017/0033404 | A1 | 2/2017 | Strand et al. |
| 2017/0141440 | A1 | 5/2017 | Shimanuki et al. |
| 2018/0006329 | A1 | 1/2018 | Xiao et al. |
| 2018/0254480 | A1 | 9/2018 | Kamo et al. |
| 2018/0316068 | A1 | 11/2018 | Park et al. |
| 2019/0165419 | A1* | 5/2019 | Moriishi ............ H01M 12/06 |
| 2020/0044285 | A1* | 2/2020 | Su ............ H01M 10/0568 |
| 2021/0184257 | A1 | 6/2021 | Kim et al. |

FOREIGN PATENT DOCUMENTS

| | | |
|---|---|---|
| CN | 106663837 A | 5/2017 |
| CN | 108028370 A | 5/2018 |
| CN | 108172901 A | 6/2018 |
| EP | 3163666 A1 | 5/2017 |
| EP | 3340361 A1 | 6/2018 |
| EP | 3783722 A1 | 2/2021 |
| JP | H07169505 A | 7/1995 |
| JP | 2012182071 A | 9/2012 |
| JP | 2012216562 A | 11/2012 |
| JP | 2015149250 A | 8/2015 |
| JP | 2018504759 A | 2/2018 |
| KR | 20080047642 A | 5/2008 |
| KR | 20170028874 A | 3/2017 |
| WO | 2020055180 A1 | 3/2020 |

OTHER PUBLICATIONS

International Search Report for Application No. PCT/KR2019/011857 mailed Dec. 23, 2019, 2 pages.

Noda et al., "A New Concept for Lithium Primary Cells Using Poly(Carbon Monofluoride) Cathode—The Effect of Quinone Compounds as an Electrolyte Additive," ECS Transactions, May 1, 2009, pp. 223-228, vol. 16, No. 35.

* cited by examiner

NON-AQUEOUS ELECTROLYTE SOLUTION FOR LITHIUM SECONDARY BATTERY AND LITHIUM SECONDARY BATTERY INCLUDING THE SAME

CROSS-REFERENCE TO RELATED APPLICATIONS

The present application is a national phase entry under 35 U.S.C. § 371 of International Application No. PCT/KR2019/011857, filed on Sep. 11, 2019, which claims priority from Korean Patent Application No. 2018-0108960, filed on Sep. 12, 2018, the disclosures of which are incorporated by reference herein.

TECHNICAL FIELD

The present invention relates to a non-aqueous electrolyte solution for a lithium secondary battery and a lithium secondary battery including the same.

BACKGROUND ART

There is a need to develop technology for efficiently storing and utilizing electrical energy as personal IT devices and computer networks are developed with the development of information society and the accompanying dependency of society as a whole on the electrical energy is increased.

Among the technologies developed for this purpose, a technology based on secondary batteries is the most suitable technology for various applications. Since a secondary battery may be miniaturized to be applicable to a personal IT device and may be applied to an electric vehicle and a power storage device, there emerges an interest in the secondary battery. Among these secondary battery technologies, lithium ion batteries, which are battery systems having the theoretically highest energy density, are in the spotlight, and are currently being used in various devices.

Unlike the early days when lithium metal was directly applied to the system, the lithium ion battery system is being realized as a system in which lithium metal is not directly used in the battery. That is, the lithium ion battery is largely composed of a positive electrode formed of a transition metal oxide containing lithium, a negative electrode formed of a carbon-based material capable of storing lithium and an alloy-based material such as silicon, an electrolyte solution that becomes a medium for transferring lithium ions, and a separator.

A significant amount of research on the electrolyte solution for a lithium ion battery has been conducted while the electrolyte solution for a lithium ion battery is known as a component that greatly affects stability and safety of the battery.

The electrolyte solution is composed of a lithium salt, an organic solvent dissolving the lithium salt, and a functional additive. $LiPF_6$, $LiBF_4$, LiFSI (lithium bis(fluorosulfonyl) imide, $LiN(SO_2F)_2$), LiTFSI (lithium bis(trifluoromethanesulfonyl) imide, $LiN(SO_2CF_3)_2$), or LiBOB (lithium bis(oxalate) borate, $LiB(C_2O_4)_2$) is being used as the lithium salt. Also, with respect to the organic solvent, a carbonate-based organic solvent, an ester-based organic solvent, or an ether-based organic solvent is being used.

With respect to the lithium ion battery, an increase in resistance and a decrease in capacity during charge and discharge or storage at high temperatures have been suggested as a serious problem in degradation of performance, and one of causes of the problem suggested is a side reaction caused by deterioration of the electrolyte solution at high temperatures, particularly deterioration due to decomposition of the lithium salt at high temperatures. In a case in which a by-product of the lithium salt is activated at high temperatures and then decomposes films formed on surfaces of the positive electrode and the negative electrode, there is a problem of decreasing passivation ability of the film, and, as a result, this may cause additional decomposition of the electrolyte solution and accompanying self-discharge.

Particularly, a graphite-based negative electrode is mostly used as the negative electrode of the lithium ion battery, wherein an operating potential of graphite is 0.3 V (vs. $Li/Li^+$) or less which is lower than an electrochemical potential window of an electrolyte solution used in the lithium ion battery. Thus, the electrolyte solution is reduced and decomposed before the negative electrode, and the reduced and decomposed product forms a solid electrolyte interphase (hereinafter, referred to as "SEI") that transmits lithium ions, but suppresses the additional decomposition of the electrolyte solution.

If the SEI does not have sufficient passivation ability to such an extent that it may suppress the additional decomposition of the electrolyte solution, the electrolyte solution is additionally decomposed during storage to cause self-discharge of the charged graphite, and, as a result, a phenomenon occurs in which a potential of the entire battery is reduced.

One of factors that may affect the passivation ability is HF and $PF_5$ which are produced by pyrolysis of $LiPF_6$, a lithium salt widely used as an electrolyte salt. While the film or the surface of the electrode is degraded due to an acid attack, dissolution of transition metal occurs at the positive electrode to increase resistance, and capacity may be reduced by loss of redox centers. Also, since the metal ions dissolved are electrodeposited on the negative electrode, irreversible capacity is increased by consumption of electrons due to the electrodeposition of the metal and the additional decomposition of the electrolyte, and thus, cell capacity may not only be reduced, but also the resistance may be increased and the graphite negative electrode may be self-discharged.

Thus, a major solution may be the suppression of damage to the film by introducing an electrolyte solution additive containing double or triple bonds that may be reduction-decomposed well, or introducing an additive capable of scavenging HF and $PF_5$, decomposition products of $LiPF_6$, i.e., a lithium salt, which are formed due to heat/moisture, in order to maintain the passivation ability of the SEI at high temperatures.

Therefore, it is urgent to propose and introduce an additive capable of eliminating a cause of the degradation of the battery at high temperatures by scavenging the by-product formed due to the decomposition of the lithium salt.

DISCLOSURE OF THE INVENTION

Technical Problem

An aspect of the present invention provides a non-aqueous electrolyte solution for a lithium secondary battery which includes a non-aqueous electrolyte solution additive having an excellent effect of scavenging HF and $PF_5$.

Another aspect of the present invention provides a lithium secondary battery including the non-aqueous electrolyte solution for a lithium secondary battery.

Technical Solution

According to an aspect of the present invention, there is provided a non-aqueous electrolyte solution for a lithium secondary battery including a lithium salt; an organic solvent; and an additive, wherein the additive includes a compound represented by Formula 1.

(Formula 1)

In Formula 1, $R_1$ to $R_3$ are each independently a substituted or unsubstituted alkyl group having 1 to 5 carbon atoms.

According to another aspect of the present invention, there is provided a lithium secondary battery including a positive electrode including a positive electrode active material; a negative electrode including a negative electrode active material; a separator disposed between the negative electrode and the positive electrode; and the non-aqueous electrolyte solution for a lithium secondary battery according to the present invention.

Advantageous Effects

Since a compound represented by Formula 1, as a Lewis base-based material included in a non-aqueous electrolyte solution of the present invention, prevents degradation of a film on a surface of a positive electrode by scavenging Lewis acids, such as HF and $PF_5$, formed as decomposition products of a lithium salt ($LiPF_6$), metal dissolution from the positive electrode may be suppressed. Also, accordingly, additional electrolyte decomposition and an increase in resistance of a negative electrode may be suppressed. Thus, if the non-aqueous electrolyte solution of the present invention including the compound represented by Formula 1 is used, a lithium secondary battery having reduced resistance and improved capacity characteristics may be achieved.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

Passivation ability of a solid electrolyte interphase (SEI) formed by decomposition of an electrolyte solution on a surface of positive/negative electrode is a major factor that greatly affects high-temperature storage performance. HF and $PF_5$, formed by pyrolysis of $LiPF_6$, a lithium salt widely used in a lithium ion battery, are known as one of factors that degrade a film. If the surface of the positive electrode is degraded by attack of the acid, transition metal dissolution occurs to increase surface resistance of the electrode due to a change in local structure of the surface, and capacity may be reduced because redox centers are lost to reduce theoretical capacity. Also, since the dissolved metal ions are electrodeposited on the negative electrode reacting in a strong reduction potential range to consume electrons and destruct the film to expose the surface of the electrode, additional electrolyte decomposition may occur to increase resistance of the negative electrode and irreversible capacity, and thus, capacity of a cell may be continuously reduced.

Thus, in order to suppress the degradation of a battery, the present invention attempts to provide a lithium secondary battery in which metal dissolution from the positive electrode is suppressed through prevention of the degradation of the film on the surface of the positive electrode by including a non-aqueous electrolyte solution including a non-aqueous electrolyte solution additive of a Lewis base material capable of scavenging $PF_5$ or HF which is formed in the electrolyte solution.

Non-aqueous Electrolyte Solution

First, in an embodiment of the present invention, provided is a non-aqueous electrolyte solution for a lithium secondary battery including a lithium salt; an organic solvent; and an additive, wherein the additive includes a compound represented by the following Formula 1.

(Formula 1)

In Formula 1, $R_1$ to $R_3$ are each independently a substituted or unsubstituted alkyl group having 1 to 5 carbon atoms.

(1) Lithium Salt

Any lithium salt typically used in an electrolyte solution for a lithium secondary battery may be used as the lithium salt without limitation, and, for example, the lithium salt may include $Li^+$ as a cation, and may include at least one selected from the group consisting of F⁻, Cl⁻, Br⁻, I⁻, NO₃⁻, N(CN)₂⁻, BF₄⁻, ClO₄⁻, B₁₀Cl₁₀⁻, AlCl₄⁻, AlO₄⁻, PF₆⁻, CF₃SO₃⁻, CH₃CO₂⁻, CF₃CO₂⁻, AsF₆⁻, SbF₆⁻, CH₃SO₃⁻, (CF₃CF₂SO₂)₂N⁻, (CF₃SO₂)₂N⁻, (FSO₂)₂N⁻, BF₂C₂O₄⁻, BC₄O₈⁻, PF₄C₂O₄⁻, PF₂C₄O₈⁻, (CF₃)₂PF₄⁻, (CF₃)₃PF₃⁻, (CF₃)₄PF₂⁻, (CF₃)₅PF⁻, (CF₃)₆P⁻, C₄F₉SO₃⁻, CF₃CF₂SO₃⁻, CF₃CF₂(CF₃)₂CO⁻, (CF₃SO₂)₂CH⁻, CF₃(CF₂)₇SO₃⁻, and SCN⁻ as an anion.

Specifically, the lithium salt may include a single material selected from the group consisting of LiCl, LiBr, LiI, LiBF₄, LiClO₄, LiB₁₀Cl₁₀, LiAlCl₄, LiAlO₄, LiPF₆, LiCF₃SO₃, LiCH₃CO₂, LiCF₃CO₂, LiAsF₆, LiSbF₆, LiCH₃SO₃, LiBETI (lithium bisperfluoroethanesulfonimide, LiN(SO₂CF₂CF₃)₂), LiTFSI (lithium bis(trifluoromethanesulfonyl) imide, LiN (SO₂CF₃)₂), and LiFSI (lithium bis(fluorosulfonyl) imide, LiN (SO₂F)₂), or a mixture of two or more thereof. In addition to them, any lithium salt commonly used in an electrolyte solution of a lithium secondary battery may be used without limitation.

The lithium salt may be appropriately changed in a normally usable range, but may be included in a concentration of 0.8 M to 3.0 M, for example, 1.0 M to 3.0 M in the electrolyte solution to obtain an optimum effect of forming a film for preventing corrosion of a surface of an electrode.

If the concentration of the lithium salt is less than 0.8 M, since mobility of lithium ions is reduced, an effect of improving cycle characteristics during high-temperature storage is insignificant, and, if the concentration of the lithium salt is greater than 3.0 M, since viscosity of the non-aqueous electrolyte solution is excessively increased, impregnability of the non-aqueous electrolyte solution may be reduced and a film-forming effect may be reduced.

(2) Organic Solvent

Various organic solvents typically used in a lithium electrolyte may be used as the organic solvent without limitation. For example, the organic solvent may include a cyclic carbonate-based organic solvent, a linear carbonate-based organic solvent, or a mixed organic solvent thereof.

The cyclic carbonate-based organic solvent is an organic solvent which may well dissociate the lithium salt in the electrolyte due to high permittivity as a highly viscous organic solvent, wherein specific examples of the cyclic carbonate-based organic solvent may be at least one organic solvent selected from the group consisting of ethylene carbonate (EC), propylene carbonate (PC), 1,2-butylene carbonate, 2,3-butylene carbonate, 1,2-pentylene carbonate, 2,3-pentylene carbonate, and vinylene carbonate, and, among them, the cyclic carbonate-based organic solvent may include at least one of ethylene carbonate and propylene carbonate (PC).

Also, the linear carbonate-based organic solvent is an organic solvent having low viscosity and low permittivity, wherein typical examples of the linear carbonate-based organic solvent may be at least one organic solvent selected from the group consisting of dimethyl carbonate (DMC), diethyl carbonate (DEC), dipropyl carbonate, ethyl methyl carbonate (EMC), methylpropyl carbonate, and ethylpropyl carbonate, and the linear carbonate-based organic solvent may specifically include ethyl methyl carbonate (EMC).

The cyclic carbonate-based organic solvent and the linear carbonate-based organic solvent may be used by being mixed in a volume ratio of 2:8 to 5:5, for example, 2:8 to 4:6.

The volume ratio of the cyclic carbonate-based organic solvent to the linear carbonate-based organic solvent may have a significant effect on improving both capacity and cycle characteristics at high temperature and room temperature during the preparation of the secondary battery, and, in a case in which the volume ratio of the cyclic carbonate-based organic solvent to the linear carbonate-based organic solvent satisfies the above range, a synergistic effect due to the mixed use of the two organic solvents may be achieved.

Also, the organic solvent may further include a linear ester-based organic solvent and/or a cyclic ester-based organic solvent in the cyclic carbonate-based organic solvent and/or the linear carbonate-based organic solvent to prepare a non-aqueous electrolyte solution having high ionic conductivity.

The linear ester-based organic solvent may include at least one of alkyl acetate or alkyl propionate.

The alkyl acetate may include at least one of methyl acetate, ethyl acetate, and propyl acetate. Also, the alkyl propionate may include at least one selected from the group consisting of methyl propionate, ethyl propionate, propyl propionate, and butyl propionate. Specifically, the linear ester-based organic solvent may include alkyl propionate having higher high-voltage stability and thermal stability than alkyl acetate.

Furthermore, the cyclic ester-based organic solvent may include at least one of γ-butyrolactone, γ-valerolactone, γ-caprolactone, σ-valerolactone, and ε-caprolactone.

The organic solvent may be used by adding an organic solvent typically used in an electrolyte solution for a lithium secondary battery without limitation, if necessary. For example, the organic solvent may further include at least one organic solvent selected from an ether-based organic solvent, an amide-based organic solvent, and a nitrile-based organic solvent.

(3) Additive (1)

The non-aqueous electrolyte solution for a lithium secondary battery of the present invention may include a compound represented by the following Formula 1 as an additive.

(Formula 1)

In Formula 1,
R₁ to R₃ are each independently a substituted or unsubstituted alkyl group having 1 to 5 carbon atoms.

Since the compound represented by Formula 1 may not suppress decomposition of anions, such as PF₆⁻ of the lithium salt, but contains a carbonyl group (C=O) acting as a Lewis base in its structure, the compound represented by Formula 1 may be combined with a Lewis acid, such as HF and PF₅, formed by the decomposition of the lithium salt to scavenge the Lewis acid. Thus, since the degradation of the film on the surface of the positive electrode, which is caused by the Lewis acid, may be suppressed, the transition metal dissolution from the positive electrode may be suppressed and a degradation behavior due to a chemical reaction of the film formed on the surface of the positive/negative electrode may be suppressed. Also, a damage to the film on the surface of the negative electrode by electrodeposition of the dissolved metal ions on the negative electrode may be prevented and additional electrolyte solution decomposition may be prevented. Furthermore, since the compound repre- sented by Formula 1 of the present invention may act as an anion receptor in the non-aqueous electrolyte solution to prevent a side reaction caused by a by-product of the lithium salt, for example, a LiF salt, the compound represented by Formula 1 may prevent a decrease in ionic conductivity and the number of free $Li^+$ ions to suppress an increase in resistance of the battery and improve battery capacity. Furthermore, the compound represented by Formula 1 may act as an oxygen scavenger that scavenges an oxygen radical by a chemical reaction such as Reaction Formula 1 below (see J. Kundu et al., Mutation Research, 768 (2014) 22-34). Thus, in a case in which the compound represented by Formula 1 is included as the electrolyte solution additive, since the compound represented by Formula 1 may suppress a side reaction between oxygen radicals and the electrolyte solution by scavenging the oxygen radicals generated from the positive electrode during high-temperature storage, the compound represented by Formula 1 may effectively improve a swelling phenomenon of the lithium secondary battery during high-temperature storage by preventing gas generation caused by the side reaction of the electrolyte solution.

In the compound represented by Formula 1, $R_1$ and $R_2$ may each independently be a substituted or unsubstituted alkyl group having 1 to 3 carbon atoms, and $R_3$ may be a substituted or unsubstituted alkyl group having 1 or 2 carbon atoms.

Specifically, the compound represented by Formula 1 may include at least one selected from the group consisting of compounds represented by Formulae 1a and 1b below.

(Formula 1a)

[Reaction Formula 1]

Glutathionylated-thymoquinone

1. NADPH CYP reductase
2. NADH CYP-b5 reductase
3. NADH-ubiqionone oxidoreductase
4. NADPH quinone oxidoreductase (NQO)

(Formula 1b)

The compound represented by Formula 1 may be included in an amount of 0.01 wt % to 1.0 wt %, particularly 0.2 wt % to 0.9 wt %, and more particularly 0.3 wt % to 0.9 wt % based on a total weight of the non-aqueous electrolyte solution.

In a case in which the compound represented by Formula 1 is included in an amount within the above range, since an SEI stabilization effect or metal dissolution suppression effect is excellent and an increase in resistance of the film due to the decomposition of the additive is effectively controlled, a secondary battery having improved overall performance may be prepared. Particularly, in a case in which the compound represented by Formula 1 is included in an amount of 0.2 wt % to 0.9 wt %, since an effect of scavenging the pyrolysis products of the salt and an effect of suppressing the increase in the resistance of the battery are excellent, capacity characteristics of the battery may be further improved.

(4) Additive for Forming SEI

The non-aqueous electrolyte solution of the present invention may further include an additive for forming an SEI, if necessary. The additive for forming an SEI, which may be used in the present invention, may include at least one additional additive selected from the group consisting of a sultone-based compound, a halogen-substituted carbonate-based compound, a nitrile-based compound, a cyclic sulfite-based compound, and a cyclic carbonate-based compound.

The sultone-based compound may include at least one compound selected from the group consisting of 1,3-propane sultone (PS), 1,4-butane sultone, ethane sultone, 1,3-propene sultone (PRS), 1,4-butene sultone, and 1-methyl-1,3-propene sultone. The sultone-based compound may be included in an amount of 0.3 wt % to 5 wt %, for example, 1 wt % to 5 wt % based on the total weight of the non-aqueous electrolyte solution. In a case in which the amount of the sultone-based compound in the non-aqueous electrolyte solution is greater than 5 wt %, since a thick film may be formed due to the excessive amount of the additive, an increase in resistance and a degradation of output may occur.

Also, the halogen-substituted carbonate-based compound may include fluoroethylene carbonate (FEC), and may be included in an amount of 5 wt % or less based on the total weight of the non-aqueous electrolyte solution. In a case in which the amount of the halogen-substituted carbonate-based compound is greater than 5 wt %, cell swelling inhibition performance may be degraded.

Furthermore, the nitrile-based compound may include at least one compound selected from the group consisting of succinonitrile (SN), adiponitrile (Adn), acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

The nitrile-based compound may be included in an amount of 5 wt % or less based on the total weight of the non-aqueous electrolyte solution, and, in a case in which the amount of the nitrile-based compound is greater than 5 wt %, since the resistance may be increased due to an increase in the film formed on the surface of the electrode, battery performance may be degraded.

Also, the cyclic sulfite-based compound may include ethylene sulfite, methylethylene sulfite, ethylethylene sulfite, 4,5-dimethylethylene sulfite, 4,5-diethylethylene sulfite, propylene sulfite, 4,5-dimethylpropylene sulfite, 4,5-diethylpropylene sulfite, 4,6-dimethylpropylene sulfite, 4,6-diethylpropylene sulfite, and 1,3-butylene glycol sulfite, and may be included in an amount of 5 wt % or less based on the total weight of the non-aqueous electrolyte solution. In a case in which the amount of the cyclic sulfite-based compound is greater than 5 wt %, since a thick film may be formed due to the excessive amount of the additive, an increase in the resistance and a degradation of the output may occur.

Also, the cyclic carbonate-based compound may include vinylene carbonate (VC) or vinyl ethylene carbonate, and may be included in an amount of 3 wt % or less based on the total weight of the non-aqueous electrolyte solution. In a case in which the amount of the cyclic carbonate-based compound in the non-aqueous electrolyte solution is greater than 3 wt %, the cell swelling inhibition performance may be degraded.

Two types or more of the additives may be mixed and included, and a total amount of the additives included may be 20 wt % or less, for example, 10 wt % or less based on the total weight of the non-aqueous electrolyte solution. If the amount of the additives is greater than 20 wt %, there is not only a possibility that a side reaction in the non-aqueous electrolyte solution occurs excessively during charge and discharge of the battery, but also, since the additives may not be sufficiently decomposed at high temperatures, the additives may be present in the form of an unreacted material or precipitates in the non-aqueous electrolyte solution at room temperature, and, accordingly, life or resistance characteristics of the secondary battery may be degraded.

Lithium Secondary Battery

Also, in an embodiment of the present invention, there is provided a lithium secondary battery including a positive electrode, a negative electrode, a separator disposed between the positive electrode and the negative electrode, and the non-aqueous electrolyte solution for a lithium secondary battery of the present invention.

Specifically, the lithium secondary battery of the present invention may be prepared by injecting the non-aqueous electrolyte solution of the present invention into an electrode assembly which is formed by sequentially stacking a positive electrode, a negative electrode, and a separator disposed between the positive electrode and the negative electrode. In this case, those typically used in the preparation of a lithium secondary battery may all be used as the positive electrode, negative electrode, and separator which constitute the electrode assembly.

The positive electrode and the negative electrode, which constitute the lithium secondary battery of the present invention, may be prepared by a conventional method and used.

(1) Positive Electrode

First, the positive electrode may be prepared by forming a positive electrode material mixture layer on a positive electrode collector. The positive electrode material mixture layer may be prepared by coating the positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may include a lithium transition metal oxide including lithium and at least one metal selected from cobalt, manganese, nickel, or aluminum, and, specifically, the positive electrode active material may include at least one active material selected from the group consisting of a lithium cobalt oxide, a lithium-nickel-manganese-cobalt-based oxide (e.g., Li(Ni$_p$Co$_q$Mn$_{r1}$)O$_2$ (where $0<p<1$, $0<q<1$, $0<r1<1$, and $p+q+r1=1$) or Li(Ni$_{p1}$Co$_{q1}$Mn$_{r2}$)O$_4$ (where $0<p1<2$, $0<q1<2$, $0<r2<2$, and $p1+q1+r2=2$), etc.), and a lithium-manganese-based oxide which have high capacity characteristics and stability of the battery, and, for example, may include a lithium-manganese-based oxide.

The lithium cobalt-based oxide may include LiCoO$_2$. Also, the lithium-nickel-manganese-cobalt-based oxide may include Li(Ni$_{1/3}$Mn$_{1/3}$Co$_{1/3}$)O$_2$, Li(Ni$_{0.6}$Mn$_{0.2}$Co$_{0.2}$)O$_2$, Li(Ni$_{0.5}$Mn$_{0.3}$Co$_{0.2}$)O$_2$, Li(Ni$_{0.7}$Mn$_{0.15}$Co$_{0.15}$)O$_2$, and Li(Ni$_{0.8}$Mn$_{0.1}$Co$_{0.1}$)O$_2$). Furthermore, the lithium-manganese-based oxide may include LiMn$_2$O$_4$.

In addition to the lithium cobalt oxide, the lithium-nickel-manganese-cobalt-based oxide, and the lithium-manganese-based oxide, the positive electrode active material of the present invention may further include at least one lithium transition metal oxide selected from the group consisting of lithium-nickel-based oxide (e.g., LiNiO$_2$, etc.), lithium-nickel-manganese-based oxide (e.g., LiNi$_{1-Y}$Mn$_Y$O$_2$ (where $0<Y<1$), LiMn$_{2-Z}$Ni$_Z$O$_4$ (where $0<Z<2$), etc.), lithium-nickel-cobalt-based oxide (e.g., LiNi$_{1-Y1}$Co$_{Y1}$O$_2$ (where $0<Y1<1$), lithium-manganese-cobalt-based oxide (e.g., LiCo$_{1-Y2}$Mn$_{Y2}$O$_2$ (where $0<Y2<1$), LiMn$_{2-Z1}$Co$_{Z1}$O$_4$ (where $0<Z1<2$), etc.), and lithium-nickel-cobalt-transition metal (M) oxide (e.g., Li(Ni$_{p2}$Co$_{q2}$Mn$_{r3}$M$_{s2}$)O$_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0\leq S2<1$, and $p2+q2+r3+S2=1$)).

The positive electrode active material may be included in an amount of 80 wt % to 99 based on a total weight of solid content in the positive electrode slurry.

The binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene termonomer (EPDM), a sulfonated EPDM, a styrene-butadiene rubber, a fluoro rubber, various copolymers thereof, and the like.

The conductive agent may typically be added in an amount of 1 wt % to 30 wt % based on the total weight of the solid content in the positive electrode slurry.

The conductive agent is not particularly limited as long as it has conductivity without causing adverse chemical changes in the battery, and, for example, a conductive material, such as: carbon powder such as carbon black, acetylene black (or Denka black), Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include an organic solvent, such as N-methyl-2-pyrrolidone (NMP), and may be used in an amount such that desirable viscosity is obtained when the positive electrode active material as well as optionally the binder and the conductive agent are included. For example, the solvent may be included in an amount such that a concentration of the solid content in the slurry including the positive electrode active material as well as optionally the binder and the conductive agent is in a range of 50 wt % to 95 wt %, for example, 70 wt % to 90 wt %.

(2) Negative Electrode

Also, the negative electrode may be prepared by forming a negative electrode material mixture layer on a negative electrode collector. The negative electrode material mixture layer may be formed by coating the negative electrode collector with a slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Furthermore, the negative electrode active material may include at least one selected from the group consisting of lithium metal, a carbon material capable of reversibly intercalating/deintercalating lithium ions, metal or an alloy of lithium and the metal, a metal composite oxide, a material which may be doped and undoped with lithium, and a transition metal oxide.

As the carbon material capable of reversibly intercalating/deintercalating lithium ions, a carbon-based negative electrode active material generally used in a lithium ion secondary battery may be used without particular limitation, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the metal or the alloy of lithium and the metal, a metal selected from the group consisting of copper (Cu), nickel (Ni), sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn), or an alloy of lithium and the metal may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O$, $Li_xFe_2O_3$ ($0 \le x \le 1$), $Li_xWO_2$ ($0 \le x \le 1$), and $Sn_xMe_{1-x}Me'_yO_z$ (Me: manganese (Mn), Fe, Pb, or Ge; Me': Al, boron (B), phosphorus (P), Si, Groups I, II and III elements of the periodic table, or halogen; $0 < x \le 1$; $1 \le y \le 3$; $1 \le z \le 8$) may be used as the metal composite oxide.

The material, which may be doped and undoped with lithium, may include Si, $SiO_x$ ($0 < x \le 2$), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, Ra, scandium (Sc), yttrium (Y), Ti, zirconium (Zr), hafnium (Hf), rutherfordium (Rf), V, niobium (Nb), Ta, dubnium (Db), Cr, Mo, tungsten (W), seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), polonium (Po), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene monomer (EPDM), a sulfonated EPDM, a styrene-butadiene rubber, a fluoro rubber, and various copolymers thereof.

The conductive agent is a component for further improving the conductivity of the negative electrode active material, wherein the conductive agent may be added in an amount of 1 wt % to 20 wt % based on the total weight of the solid content in the negative electrode slurry. Any conductive agent may be used without particular limitation so long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as NMP and alcohol, and may be used in an amount such that desirable viscosity is obtained when the negative electrode active material as well as optionally the binder and the conductive agent are included. For example, the solvent may be included in an amount such that a concentration of the solid content in the negative electrode slurry including the negative electrode active material as well as optionally the binder and the conductive agent is in a range of 50 wt % to 95 wt %, for example, 70 wt % to 90 wt %.

(3) Separator

Also, the separator plays a role in blocking an internal short circuit between both electrodes and being impregnated with the electrolyte, wherein, after mixing a polymer resin, a filler, and a solvent to prepare a separator composition, the separator composition is directly coated on the electrode and dried to form a separator film, or, after the separator composition is cast on a support and dried, the separator may be prepared by laminating a separator film peeled from the support on the electrode.

A typically used porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

In this case, the porous separator may generally have a pore diameter of 0.01 μm to 50 μm and a porosity of 5% to 95%. Also, the porous separator may generally have a thickness of 5 μm to 300 μm.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

A non-aqueous electrolyte solution was prepared by adding 1 g of the compound of Formula 1a as an additive to 99 g of a non-aqueous organic solvent (ethylene carbonate (EC):ethyl methyl carbonate (EMC)=volume ratio of 30:70) in which 1.2 M $LiPF_6$ was dissolved (see Table 1 below).

Example 2

A non-aqueous electrolyte solution was prepared by adding 0.9 g of the compound of Formula 1a as an additive to 99.1 g of a non-aqueous organic solvent (ethylene carbonate (EC):ethyl methyl carbonate (EMC)=volume ratio of 30:70) in which 1.2 M LiPF$_6$ was dissolved (see Table 1 below).

Example 3

A non-aqueous electrolyte solution was prepared by adding 0.5 g of the compound of Formula 1a as an additive to 99.5 g of a non-aqueous organic solvent (ethylene carbonate (EC):ethyl methyl carbonate (EMC)=volume ratio of 30:70) in which 0.3 M LiPF$_6$ and 0.7 M LiFSI were dissolved (see Table 1 below).

Example 4

A non-aqueous electrolyte solution was prepared by adding 1.5 g of the compound of Formula 1a as an additive to 98.5 g of a non-aqueous organic solvent (ethylene carbonate (EC):ethyl methyl carbonate (EMC)=volume ratio of 30:70) in which 0.3 M LiPF$_6$ and 0.7 M LiFSI were dissolved (see Table 1 below).

Comparative Example 1

A non-aqueous electrolyte solution was prepared by dissolving LiPF$_6$ in a non-aqueous organic solvent, in which ethylene carbonate (EC) and ethyl methyl carbonate (EMC) were mixed in a volume ratio of 30:70, such that a concentration of the LiPF$_6$ was 1.2 M.

TABLE 1

| | Lithium salt | Organic solvent Configuration (volume ratio) | Amount (g) | Additive Formula | Amount (g) |
|---|---|---|---|---|---|
| Example 1 | 1.2M LiPF$_6$ | EC:EMC = 30:70 | 99 | 1a | 1 |
| Example 2 | 1.2M LiPF$_6$ | EC:EMC = 30:70 | 99.1 | 1a | 0.9 |
| Example 3 | 0.3M LiPF$_6$ 0.7M LiFSI | EC:EMC = 30:70 | 99.5 | 1a | 0.5 |
| Example 4 | 0.3M LiPF$_6$ 0.7M LiFSI | EC:EMC = 30:70 | 98.5 | 1a | 1.5 |
| Comparative Example 1 | 1.2M LiPF$_6$ | EC:EMC = 30:70 | 100 | — | |

Experimental Examples

Experimental Example 1

A positive electrode active material (LiMn$_2$O$_4$), a conductive agent (carbon black), and a binder (polyvinylidene fluoride (PVDF)) were added to N-methyl-2-pyrrolidone (NMP), as a solvent, at a weight ratio of 97.5:1:1.5 to prepare a positive electrode slurry. A 20 μm thick positive electrode collector (Al foil) was coated with the positive electrode slurry, dried, and roll-pressed to prepare a positive electrode.

Then, the positive electrodes were respectively introduced into 5 mL of each of the non-aqueous electrolyte solutions prepared in Examples 1 and 2 and 5 mL of the non-aqueous electrolyte solution prepared in Comparative Example 1 and stored at 60° C. for 2 weeks at a state of charge (SOC) of 0%.

Subsequently, a concentration of metal, for example, manganese (Mn) dissolved in each electrolyte solution was measured using an inductively coupled plasma atomic emission spectrophotometer (ICP-AES, ICPS-8100, manufactured by Shimadzu Corporation, RF source: 27.12 MHz, sample uptake rate: 0.8 ml/min), and amounts of the metal measured are presented in FIG. 1 below.

Figure 1:
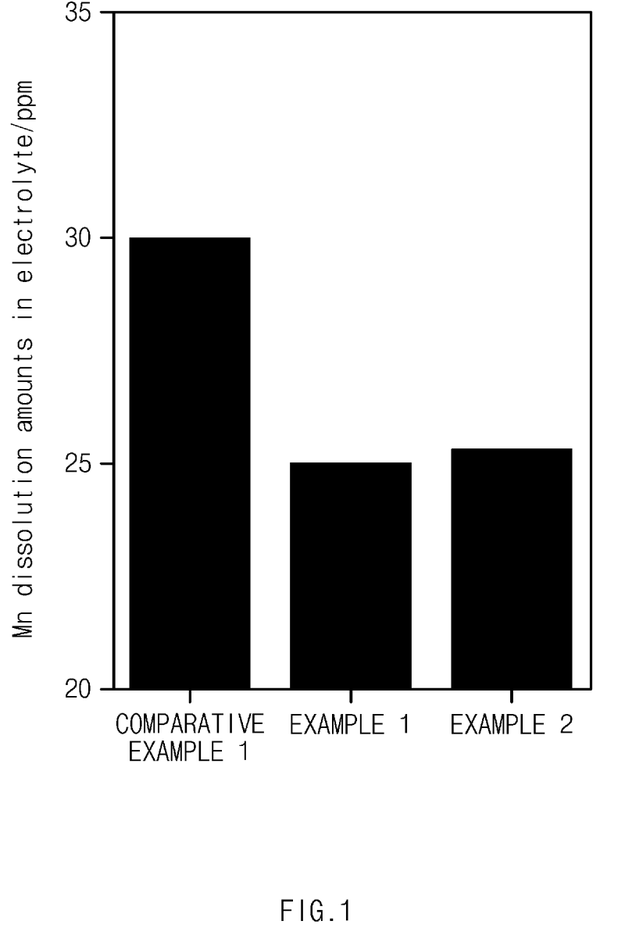
FIG. 1 is a graph illustrating the results of metal dissolution suppression effect according to Experimental Example 1 of the present invention.

Referring to FIG. 1, with respect to the non-aqueous electrolyte solutions of Examples 1 and 2 of the present invention including the additive, since the compound containing a Lewis base, which was included as the additive, may effectively scavenge HF and PF$_5$, as the decomposition products of the lithium salt which were formed at high temperatures, an effect of suppressing metal dissolution from the positive electrode was significantly improved in comparison to that of the non-aqueous electrolyte solution of Comparative Example 1 which did not include an additive, and thus, it may be confirmed that few Mn ions were detected.

Experimental Example 2

Figure 2:
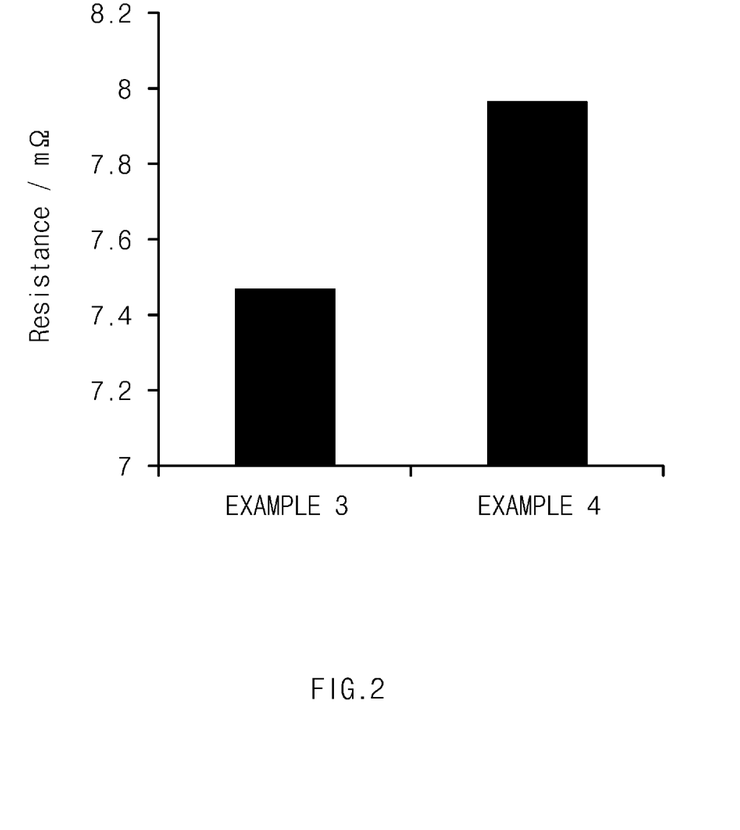
FIG. 2 is a graph illustrating resistance values calculated according to Experimental Example 2 of the present invention.

Ionic conductivities of the non-aqueous electrolyte solutions of Examples 3 and 4 were measured using a SevenExcellence S700 instrument by METTLER TOLEDO. Specifically, each of the non-aqueous electrolyte solutions prepared in Examples 3 and 4 and the non-aqueous electrolyte solution of Comparative Example 2 was filled in a bath so that a probe for measuring ionic conductivity was immersed in the bath, and the ionic conductivity was measured through the immersed probe. The measured ionic conductivity values were substituted into the following Equation 1 to calculate resistance, and the results thereof are presented in FIG. 2.

$$R=(1/\sigma)(d/A) \qquad \text{Equation 1}$$

In Equation 1,
R: resistance (mΩ)
A: electrode area of lithium secondary battery (cm$^2$)
d: thickness of separator used (distance between electrodes, cm)
σ: ionic conductivity (mS/cm)

In this case, since the ionic conductivity in the above equation is an inverse of specific resistance, it is expressed as 1/σ.

Referring to FIG. 2, it may be confirmed that resistance of the non-aqueous electrolyte solution of Example 4 including 1.5 wt % of the additive was higher than resistance of the non-aqueous electrolyte solution of Example 3 including 0.5 wt % of the additive. From this result, it may be predicted that, in a case in which the non-aqueous electrolyte solution of Example 3 with low resistance is used, output characteristics are improved in comparison to a case where the non-aqueous electrolyte solution of Example 4 is used.

The invention claimed is:
1. A lithium secondary battery comprising:
a positive electrode comprising a positive electrode active material;
a negative electrode comprising a negative electrode active material;
a separator disposed between the negative electrode and the positive electrode; and
a non-aqueous electrolyte solution,
wherein the positive electrode active material comprises at least one of a lithium cobalt oxide, a lithium-nickel-manganese-cobalt-based oxide, or a lithium-manganese-based oxide,
the non-aqueous electrolyte solution comprises a lithium salt; an organic solvent; and an additive, and
the additive comprises a compound represented by Formula 1:

(Formula 1)

wherein, in Formula 1,
$R_1$ to $R_3$ are each independently a substituted or unsubstituted alkyl group having 1 to 5 carbon atoms.

2. The lithium secondary battery of claim 1, wherein, in Formula 1, $R_1$ and $R_2$ are each independently a substituted or unsubstituted alkyl group having 1 to 3 carbon atoms, and $R_3$ is a substituted or unsubstituted alkyl group having 1 or 2 carbon atoms.

3. The lithium secondary battery of claim 1, wherein the compound represented by Formula 1 comprises at least one of compounds represented by Formulae 1a or 1b:

(Formula 1a)

(Formula 1b)

4. The lithium secondary battery of claim 1, wherein the compound represented by Formula 1 is included in an amount of 0.01 wt % to 1.0 wt % based on a total weight of the non-aqueous electrolyte solution.

5. The lithium secondary battery of claim 4, wherein the compound represented by Formula 1 is included in an amount of 0.2 wt % to 0.9 wt % based on the total weight of the non-aqueous electrolyte solution.

6. The lithium secondary battery of claim 5, wherein the compound represented by Formula 1 is included in an amount of 0.3 wt % to 0.9 wt % based on the total weight of the non-aqueous electrolyte solution.

7. The lithium secondary battery of claim 1, wherein the positive electrode active material comprises the lithium-manganese-based oxide.

8. The lithium secondary battery of claim 7, wherein the lithium-manganese-based oxide comprises $LiMn_2O_4$.

* * * * *